United States Patent [19]

Wato et al.

[11] Patent Number: 5,236,713

[45] Date of Patent: Aug. 17, 1993

[54] PREPARATION FOR INTERMITTENTLY RELEASING ACTIVE AGENT APPLICABLE TO ORAL CAVITY

[75] Inventors: Takahiko Wato; Teruo Hama; Nobuko Inoue, all of Kagawa; Yukihiro Tada, Takamatsu; Shin-ichi Hisaichi, Kagawa, all of Japan

[73] Assignee: Teikoku Seiyaku Kabushiki Kaisha, Kagawa, Japan

[21] Appl. No.: 716,689

[22] Filed: Jun. 17, 1991

Related U.S. Application Data

[63] Continuation of Ser. No. 261,005, Oct. 21, 1988, abandoned.

[30] Foreign Application Priority Data

Oct. 21, 1987 [JP] Japan .............................. 62-267221

[51] Int. Cl.$^5$ .............................................. A61F 13/00
[52] U.S. Cl. ................................... 424/443; 424/448; 424/449; 424/447
[58] Field of Search ................. 424/443, 449, 448, 447

[56] References Cited

U.S. PATENT DOCUMENTS 4,483,846 11/1984 Koide et al. ......................... 424/443
4,601,893 7/1986 Cardinal .............................. 424/438

Primary Examiner—Thurman K. Page
Assistant Examiner—Leon R. Horne
Attorney, Agent, or Firm—Birch, Stewart, Kolasch & Birch

[57] ABSTRACT

A preparation for intermittently releasing an active agent which comprises a laminated combination of a release-controlling layer and a pharmaceutically active agent-containing layer wherein one or more of pharmaceutically active agent layers are incorporated into said release-controlling layer. The preparation in accordance with the present invention can intermittently control the release of the active agent to decrease a dosage time and is applicable to the mucous membrane or gingivae within the oral cavity.

4 Claims, 3 Drawing Sheets (1)

(2)

(3)

Example 1

Example 2

Example 3

PREPARATION FOR INTERMITTENTLY RELEASING ACTIVE AGENT APPLICABLE TO ORAL CAVITY

This application is a continuation of application Ser. No. 07/261,005 filed on Oct. 21, 1988, now abandoned, the entire contents of which are incorporated herein by reference.

The present invention relates to a preparation for intermittently releasing an active agent, more particularly to a preparation for controlling release of an active agent. The preparation of the present invention has a dosage form applicable to the oral cavity and is controllable so as to intermittently release an active agent, by which the releasing time of the active agent can be shortened and further the dosage times can be decreased.

PRIOR ART

There have hitherto been known coated tablets, dry coated tablets, multilayer tablets and the like for the purpose of sustained or prolonged release of an active agent through oral administration. However, when these tablets are actually introduced into a living body, the active agent does not remain in an absorption area for a long period of time due to a difference of the moving rate of the agent within the digestive tract which differs in each individual. Therefore, the agent is often excreted out of the living body without attaining an effective blood concentration. Another defect of the conventional preparations are a poor bioavailability which is induced by sustained or prolonged release of the active agent in the preparations, as well as a drug tolerance and a chronic toxicity due to the active ingredient remaining for a long period of time in blood through prolonged release of the active ingredient.

Further, in the above conventional preparations for sustained or prolonged release of the active agent, the physiologically active agent is gradually released at a fixed and controlled rate continuously from a matrix, but it is impossible to intermittently release or to release the active agent with an interval in view of their structure. However, some physiologically active agents are produced periodically in the living body at intervals and, in some cases, periodical release of the physiological agent with an interval is desirable when administered into tissues.

BRIEF SUMMARY OF THE INVENTION

Under the circumstances, the present inventors have intensively studied an improved preparation applicable to the oral cavity in the human which is capable of intermittently releasing the active agent at intervals, and have found that the desired intermittent release of the active agent can be achieved by combining a release-controlling layer and a pharmaceutically active agent-containing layer and further incorporating a pharmaceutically active agent-containing layer into the release-controlling layer.

An object of the present invention is to provide a preparation for intermittently releasing the active agent applicable to the oral cavity which comprises a laminate of a release-controlling layer and a pharmaceutically active agent-containing layer and wherein one or more pharmaceutically active agent-containing layers are incorporated into the release-controlling layer. These and other objects and advantages of the present invention will be apparent to skilled persons from the following description.

Figure 1:
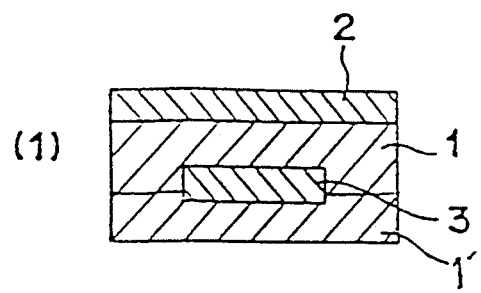
FIGS. 1 (1) to (3) illustrate sectional views of one embodiment of the preparations according to the present invention.
Figure 1:
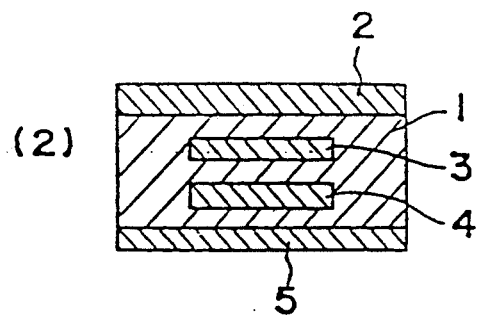
Figure 1:
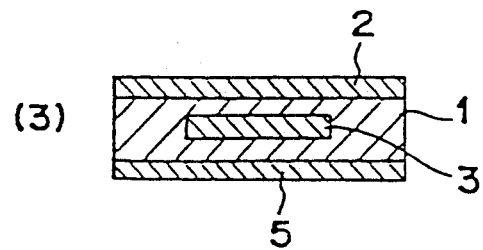

1, 1': a release-controlling layer, 2,3,4: a pharmaceutically active agent-containing layer, 5: an adhesive layer

DETAILED DESCRIPTION OF THE INVENTION

The preparation of the present invention comprises a release-controlling layer and a pharmaceutically active agent-containing layer, said release-controlling layer containing one or more pharmaceutically active agent-containing layers, and further optionally an adhesive layer.

The release-controlling layer of the present invention comprises as an essential component a water-soluble or water-swelling high molecular weight compound and optionally conventional binders, lubricants, plasticizers, coloring agents, preservatives, flavors, excipients and the like, for improving physical properties, shape, taste or smell of the preparation, which are optionally dissolved in and diluted with a suitable solvent (e.g. water, ethanol, acetone, ethyl acetate, or a mixture thereof).

The water-soluble or water-swelling high molecular weight compound of the present invention includes, for example, a cellulose derivative (e.g. methyl cellulose, ethyl cellulose, hydroxypropyl cellulose, hydroxypropyl methyl cellulose, sodium carboxymethyl cellulose, hydroxypropyl methyl cellulose phthalate, cellulose acetate phthalate, hydroxypropyl methyl cellulose acetate succinate etc.), polyacrylic acid or a salt thereof, polyvinyl pyrrolidone, polyvinyl alcohol, methoxyethylene maleic-anhydride copolymer, polyvinyl acetate, alginic acid or a salt thereof, an acrylic polymer, natural rubber, a carboxyvinyl polymer and the like, which may be used alone or in combination of two or more thereof. Particularly preferred compound is hydroxypropyl methyl cellulose acetate succinate.

The release-controlling layer of the present invention contains the water-soluble or water-swelling high molecular weight compound in an amount of from 50 to 100% by weight (hereinafter the same), preferably from 60 to 95% for preparing tablets. In this case, crystalline cellulose, carboxymethyl cellulose and the like are preferably employed as the binders in an amount of not more than 20%. Preferably, talc, magnesium stearate and the like are employed as the lubricants in an amount of not more than 20%, preferably from 2 to 10%. As the excipients, lactose, starch, aluminum silicate and the like are preferably employed in an amount of not more than 10%. In case for preparing film-shaped preparations, the release-controlling layer contains the water-soluble or water-swelling high molecular weight compound in an amount of from 50 to 95%, preferably from 60 to 85% wherein 1,3-butanediol, polyethylene glycol, triethyl citrate, propylene glycol, castor oil and the like are employed as the plasticizers in an amount of from 5 to 50%, preferably from 15 to 40%.

The pharmaceutically active agent-containing layer comprises a pharmaceutically active agent and a pharmaceutical carriers and diluents. The carriers and diluents may be conventional binders, lubricants, plasticizers, coloring agents, preservatives, flavors, excipients and the like, but preferably includes a water-soluble or water-swelling high molecular weight compound like the release-controlling layer. The pharmaceutically active agent is usually contained in the layer in an amount of 5 to 80% by weight, preferably 20 to 50% by weight, based on the whole weight of the phamaceutically active agent-containing layer.

The pharmaceutically active agent of the present invention may be any pharmaceutically active compound in so far as it can be administered orally and includes, for example, antiinflammatories and analgesics (e.g. indomethacin, diclofenac, ibuprofen, phenylbutazone, oxyphenbutazone, mepirizole, aspirin, ethenzamide, aminophylline, phenacetin etc.), antiasthmatics (e.g. salbutamol hydrosulfate etc.), antivetigo agents (dl-isoproterenol hydrochloride, difenidol hydrochloride, betahistine mesilate etc.), coronary vasodilators (isosorbide dinitrate, nitroglycerin, nifedipine etc.), antiarrhythmics (e.g. acebutolol hydrochloride, alprenolol hydrochloride, indenolol hydrochloride, oxprenolol hydrochloride, carteolol hydrochloride, propranolol hydrochloride, pindolol, disopyramide etc.), antiulcers, antimicrobials such as antibiotics (tetracycline hydrochloride, oxytetracycline, streptomycin, gentamicin, bacitracin, erythromycin, ampicillin, penicillin, etc.), and the like, which may be used alone or in combination of two or more thereof.

The preparation for intermittently releasing the active agent applicable to the oral cavity according to the present invention comprises a combination of the release-controlling layer and the pharmaceutically active agent-containing layer which is in a specific structure. The preparation of the present invention is more concretely explained with accompanying drawings which illustrate one embodiment of the preparation of the present invention.

As shown in FIGS. 1 (1) to (3), the preparation of the present invention is such that the pharmaceutically active agent-containing layer 2 is laminated onto the release-controlling layer 1, and said release-controlling layer 1 contains another one pharmaceutically active agent-containing layer 3 [see FIGS. (1) and (3)] or two pharmaceutically active agent-containing layers 3 and 4 [see FIG. 1 (2)]. When one pharmaceutically active agent-containing layer is incorporated into the release-controlling layer, the preparation has one interval in releasing the active agent, and when two pharmaceutically active agent-containing layer is incorporated into the release-controlling layer, the preparation has two intervals in releasing the active agent. In this way, the number of intervals are determined in accordance with the number of the pharmaceutically active agent-containing layers which are incorporated into the release-controlling layer. The preparation of the present invention may also be provided with a conventional adhesive layer 5 under the release-controlling layer 1 [see FIGS. 1 (2) and (3)], which enables adhesion of the preparation of the present invention onto the oral cavity. The preparation of each layer may be carried out in accordance with any conventional known method, for example, compressing or spreading and laminating.

The dosage form of the preparation of the present invention is not particularly limited in so far as it can be remained in the oral cavity and includes, for example, buccals, trouches, sublingual tablets, or another dosage forms for adhesing onto the mucous membrane or the gingivae within the oral cavity.

The preparation of the present invention can be administered via the mucous membrane or gingiviae within the oral cavity.

The preparation of the present invention prepared as mentioned above has various advantages as follows:

i) The conventional chronic toxicity or drug tolerance due to prolonged release of the drug can be avoided and at the same time there can be achieved a decrease in dosage time which is an advantage of the prolonged release preparation.

ii) By applying the preparation into the oral cavity, an effect of pH in the digestive tract and the like can be avoided and thus a stable release of the effective ingredient is obtainable.

iii) Since several times of releases of the drug can be obtained by only one administration, only one or two administration per day are sufficient though several administrations per day are required when using the conventional preparations. Therefore, it can be prevented to forget to take medicine or to take medicine at a wrong time.

iv) Many patients do not take medicine at a proper time. However, because the preparation according to the present invention one release the active agent at the time to take medicine through control of the intermittent release of drug, the treating effect of the drug can be improved more efficiently.

v) The conventional prolonged preparations tend to show a decrease of the effect of an effective ingredient during the night in spite of the prolonged activity of the preparation. On the contrary, the use of the preparation of the present invention can release the effective ingredient even in the nighttime and thus is also useful for preventing attacks of angina pectoris which occur at dawn.

The present invention is illustrated by the following Examples but should not be construed to be limited thereto.

EXAMPLE 1

The preparation shown in FIG. 1 (1) is prepared as follows:

(a) Composition for release-controlling layer 1:

Hydroxypropyl methyl cellulose acetate succinate (15 g), methoxyethylene maleic-anhydride copolymer (Gantlet®, G.A.F. Corporation) (5 g), talc (1 g) and magnesium stearate (0.1 g) are mixed uniformly.

(b) Composition for release-controlling layer 1':

Hydroxypropyl methyl cellulose acetate succinate (20 g)

(c) Composition for pharmaceutically active agent-containing layer (outer layer 2 and inner nuclear layer 3):

Polyvinylpyrrolidone (4 g), lactose (1 g) and isosorbide dinitrate (5 g) are mixed uniformly.

(d) Preparation:

The composition for pharmaceutically active agent-containing layer prepared in the above process (c) (10 mg) is put in a tabletting machine (diameter: 5 mm) and a pressure of 20 kg/cm$^2$ is applied to give an inner nuclear layer 3. Then the composition for release-controlling layer 1' (90 mg), the above inner nuclear layer 3, the composition for release-controlling layer 1 (110 mg) and the composition for pharmaceutically active agent-containing layer (outer layer 2) (10 mg) are laminated in this order in a tabletting machine (diameter: 10 mm) and a pressure of 400 kg/cm² is applied to prepare tablets.

EXAMPLE 2

The preparation shown in FIG. 1 (2) is prepared as follows:

(a) Composition for release-controlling layer 1:

Hydroxypropylmethyl cellulose acetate succinate (100 g) and magnesium stearate (0.2 g) are mixed uniformly.

(b) Composition for pharmaceutically active agent-containing layer (I) (inner nuclear layers 3 and 4):

Polyvinylpyrrolidone (9 g), crystalline cellulose (1 g) and nitroglycerin (10% in lactose) (10 g) are mixed uniformly.

(c) Composition for pharmaceutically active agent-containing layer (II) (outer layer 2):

Lactose (15 g), nitroglycerin (10% in lactose) (5 g) and sodium carboxymethyl cellulose (2 g) are mixed uniformly.

(d) Composition for adhesive layer 5:

Sodium alginate (35 g, polyacrylic acid (40 g) and gelatin (25 g) are mixed uniformly.

(e) Preparation:

The composition for pharmaceutically active agent-containing layer (I) (10 mg) are each put in a tabletting machine (diameter: 5 mm) and a pressure of 20 kg/cm² is applied to give inner nuclear layer tablets 3 and 4, respectively. Then the composition for adhesive layer 5 (20 mg), the composition for release-controlling layer 1 (110 mg), the above nuclear layer tablet 4, the composition for release-controlling layer 1 (80 mg), the above nuclear layer tablet 3, the composition for release-controlling layer 1 (75 mg) and the composition for pharmaceutically active agent-containing layer (II) (15 mg) are laminated in this order in a tabletting machine (diameter: 10 mm) and a pressure of 400 kg/cm² is applied to prepare tablets.

EXAMPLE 3

The preparation shown in FIG. 1 (3) is prepared as follows:

(a) Composition for release-controlling layer 1:

Hydroxypropyl methyl cellulose acetate succinate (10 g) and methacrylic acid copolymer (manufactured by Rohm Pharmer Co. Ltd., Eudragit® S 100, 5.5 g) are dissolved in ethanol (80 ml), purified water (20 ml), triethyl citrate (8 ml) and polyethylene glycol 400 (2 ml).

(b) Composition for pharmaceutically active agent-containing layer (I) (outer layer 2):

Polyvinylpyrrolidone (20 g) and salbutamol sulfate (2 g) are dissolved in ethanol (100 ml), purified water (40 ml) and 1,3-butanediol (5 ml).

(c) Composition for pharmaceutically active agent-containing layer (II) (inner nuclear layer 3):

Hydroxypropyl methyl cellulose (15 g) and salbutamol sulfate (1 g) are dissolved in ethanol (50 ml), purified water (50 ml) and propylene glycol (10 ml).

(d) Composition for adhesive layer 5:

Hydroxypropyl methyl cellulose (20 g) and hydroxypropyl cellulose (5 g) are dissolved in ethanol (100 ml), purified water (100 ml) and polyethylene glycol 400 (5 ml).

(e) Preparation:

Firstly the composition mixture for the adhesive layer 5 is spread on a release paper and is dried to form film. Thereafter the composition mixture for the lower part of the release-controlling layer 1 is spread on the above formed film and is dried to form film. Then the pharmaceutically active agent-containing layer (II) (inner nuclear layer 3), which is separately prepared to form film in the same way as mentioned above, is punched in a diameter of 5 mm which is placed on the above release-controlling layer with pressure. On the resulting laminated product are successively spread the composition mixture for the upper part of the release-controlling layer 1 and the the composition mixture for the pharmaceutically active agent-containing layer (I) (outer layer 2) and are dried to form film. Thereafter the formed product is punched in 1.5 cm × 2 cm to give a film-shaped preparation with total thickness of 1.1 mm.

Figure 2:
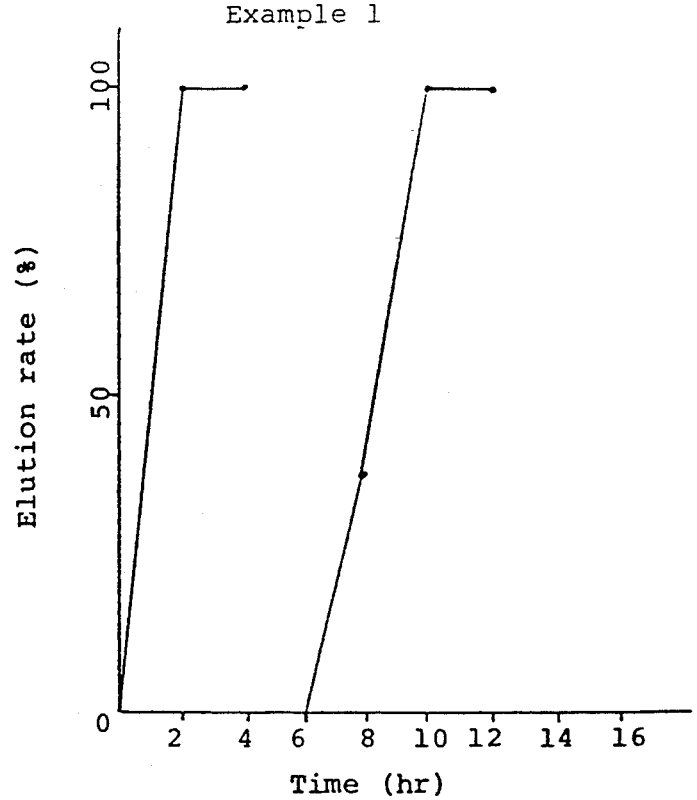
FIGS. 2 to 4 are graphs showing results in agent release test in Examples 1 to 3, respectively.
Figure 3:
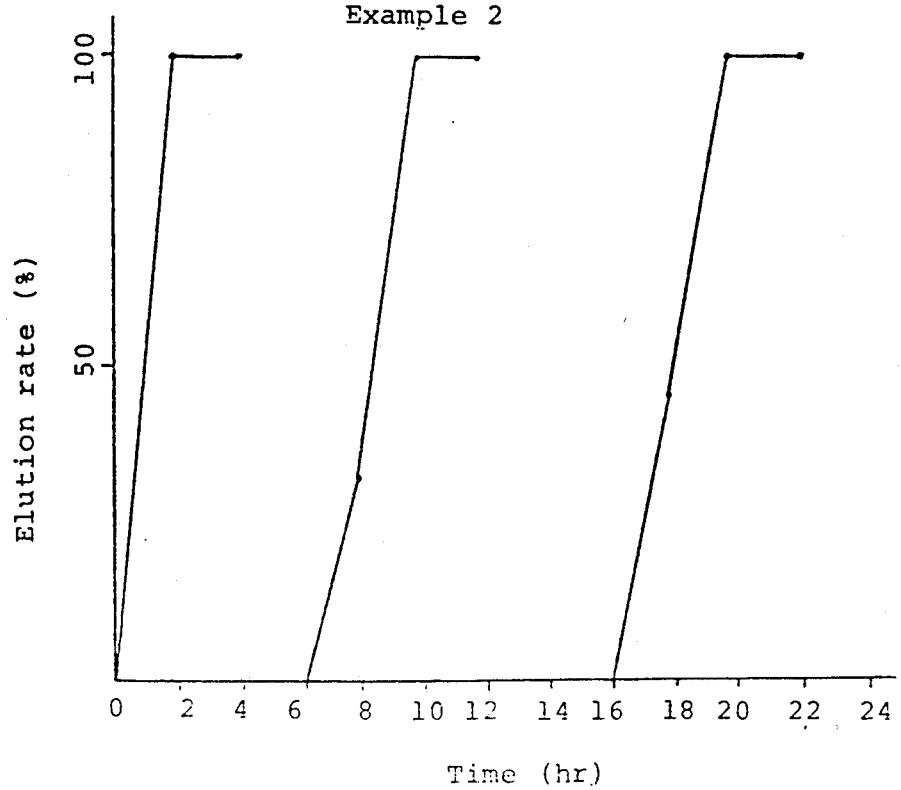
Figure 4:
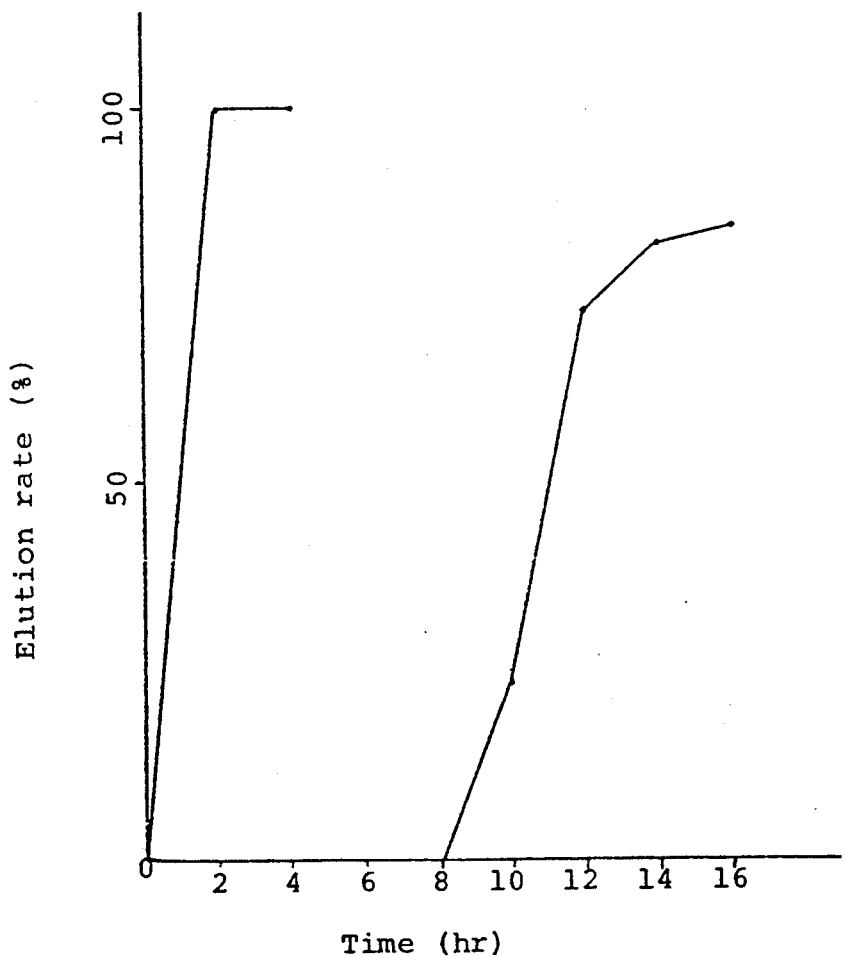

Test for the elution was carried out on the above preparations of Examples 1 to 3 in accordance with Japan Pharmacopoeia XI rotating basket method. The results are shown in FIGS. 2 to 4.

What is claimed is:

1. A controlled release preparation for periodic release of an active agent at intervals which comprises:
   (1) a controlled release layer containing no pharmaceutically active agent and which comprises a water-soluble high molecular weight compound selected from the group consisting of methyl cellulose, hydroxypropyl methyl cellulose, sodium carboxymethyl cellulose, polyacrylic acid or a salt thereof, polyvinyl alcohol, alginic acid or a salt thereof, carboxyvinyl polymer, hydroxypropyl methyl cellulose phthalate, hydroxypropyl methyl cellulose acetate succinate, and methoxyethylene maleic anhydride copolymer or a mixture of said water-soluble high molecular weight compound and a water-swelling high molecular weight compound selected from the group consisting of ethyl cellulose, cellulose acetate phthalate, polyvinyl acetate, acrylic polymer and natural rubber; and
   (2) at least two discrete pharmaceutically active agent-containing layers, said pharmaceutically active agent-containing layers which comprise said water-soluble high molecular weight compound and a pharmaceutically active agent;
   wherein a first of said pharmaceutically active agent-containing layers is disposed and laminated at a surface of said controlled release layer; and
   wherein additional of said pharmaceutically active agent-containing layers are incorporated into said controlled release layer.

2. The preparation of claim 1, wherein the water-soluble high molecular weight compound is a member selected from hydroxypropyl methyl cellulose acetate succinate and methoxyethylene maleic anhydride copolymer.

3. The preparation of claim 1, wherein water-swelling high molecular weight compound is a member selected from acrylic polymer and natural rubber.

4. The preparation of claim 1, further comprising an adhesive layer in contact with a surface of said controlled release layer.

* * * * *